United States Patent
Savarese

(10) Patent No.: US 12,412,216 B2
(45) Date of Patent: Sep. 9, 2025

(54) DIGITAL RESILIENCE MARKETPLACE PLATFORM AND METHOD THEREOF

(71) Applicant: Swiss Reinsurance Company Ltd., Zurich (CH)

(72) Inventor: Domenico Savarese, Richterswil (CH)

(73) Assignee: Swiss Reinsurance Company Ltd., Zurich (CH)

( * ) Notice: Subject to any disclaimer, the term of this patent is extended or adjusted under 35 U.S.C. 154(b) by 868 days.

(21) Appl. No.: 17/337,143

(22) Filed: Jun. 2, 2021

(65) Prior Publication Data

US 2022/0138819 A1 May 5, 2022

Related U.S. Application Data

(63) Continuation of application No. PCT/EP2020/081115, filed on Nov. 5, 2020.

(51) Int. Cl.
| | |
|---|---|
| *G06Q 40/08* | (2012.01) |
| *G06Q 30/0601* | (2023.01) |
| *G16H 20/60* | (2018.01) |

(52) U.S. Cl.
CPC ......... *G06Q 40/08* (2013.01); *G06Q 30/0609* (2013.01); *G16H 20/60* (2018.01)

(58) Field of Classification Search
CPC ......... G06Q 30/06–0645; G06Q 30/08; G06Q 50/01; G06Q 40/08; G16H 20/60; G16Y 10/00–90
See application file for complete search history.

(56) References Cited

U.S. PATENT DOCUMENTS

| | | | | |
|---|---|---|---|---|
| 7,831,451 B1 * | 11/2010 | Morse | ............ | G06Q 40/08 |
| | | | | 705/2 |
| 10,679,294 B1 * | 6/2020 | Lanzrath | ............ | G16H 10/40 |
| 11,354,749 B2 * | 6/2022 | Jiang | ............ | G06N 20/10 |
| 11,580,474 B2 * | 2/2023 | Perl | ............ | G06Q 50/40 |
| 11,615,473 B2 * | 3/2023 | Shakfeh | ............ | G16H 50/70 |
| | | | | 705/2 |

(Continued)

FOREIGN PATENT DOCUMENTS

| | | | |
|---|---|---|---|
| AU | 2019100373 A4 * | 5/2019 | |
| WO | WO 2010/138932 A1 * | 1/2012 | ............ G06F 19/00 |

(Continued)

*Primary Examiner* — Adam L Levine
(74) *Attorney, Agent, or Firm* — Oblon, McClelland, Maier & Neustadt, L.L.P.

(57) ABSTRACT

A digital marketplace platform providing an automated, multi-channel, end-to-end, digital marketplace platform providing fully automated, end-to-end risk-assessment and risk-transfer processes by configuring, launching and processing of customized insurance and/or reinsurance products and services offered for B2B and B2C users. Each individual and service provided on the Marketplace is automatically rated on its contribution to a resilience score of the consumers that purchase products on the Marketplace and benefits from the marketplace's services. In L&H risk-transfer, the resilience score, inter alia, measures and rates the current health status of individuals, and their likelihood to purchase insurance protection or start/keep behaviors that improve their health status, dynamically reassessed throughout the term of the risk-transfer, i.e. its lifetime, by the digital platform.

32 Claims, 4 Drawing Sheets

(56) References Cited

U.S. PATENT DOCUMENTS

| | | | |
|---|---|---|---|
| 11,868,684 B2* | 1/2024 | Fasano | G06Q 10/20 |
| 2005/0102172 A1* | 5/2005 | Sirmans, Jr. | G06Q 40/02 |
| | | | 705/4 |
| 2008/0114620 A1* | 5/2008 | Donnelli | G06Q 40/08 |
| | | | 705/4 |
| 2011/0022420 A1* | 1/2011 | Morse | G16H 10/60 |
| | | | 705/4 |
| 2018/0218453 A1* | 8/2018 | Crabtree | G06N 5/022 |
| 2021/0295446 A1* | 9/2021 | Mangold | G06Q 10/04 |

FOREIGN PATENT DOCUMENTS

| | | | | |
|---|---|---|---|---|
| WO | WO-2014155106 A1 * | 10/2014 | | G06Q 40/00 |
| WO | WO-2017036515 A1 * | 3/2017 | | G06Q 40/08 |
| WO | WO-2017220140 A1 * | 12/2017 | | G06N 20/10 |
| WO | WO-2019084061 A1 * | 5/2019 | | G06N 5/022 |

* cited by examiner

DIGITAL RESILIENCE MARKETPLACE PLATFORM AND METHOD THEREOF

CROSS REFERENCE TO RELATED APPLICATION

The present application is a continuation application of International Patent Application No. PCT/EP2020/081115, filed on Nov. 5, 2020, the content of which is hereby incorporated by reference in its entirety.

FIELD OF THE INVENTION

The present invention relates to systems and methods in the field of life/health and/or property/casualty risk assessment and risk-transfer (including UW and claim handling), covering the whole process by providing a fully automated insurer/carrier (and consumer) platform. In particular, the invention relates to the field of digital platforms, simulation and digital twin technology. A core feature is provided by a measured quantitative risk index measure of the automated digital marketplace platform, which is in the present invention given by the inventive measured personal (respectively individual) resilience score. Thus, the present invention further relates to intelligent, automated optimization technologies for a digital marketplace platform enabled to securely steer, monitor and adapt/optimize of risk-transfer solution in B2B and B2C interaction on the digital marketplace environment. More particularly, it relates to systems for automation of underwriting, risk management, risk-transfer and risk portfolio steering and signaling involving an improved composing and configuring of products for a user interactively based on a measured quantity of the personal resilience score.

BACKGROUND OF THE INVENTION

Automated or semi-automated risk-transfer systems, typically interacting with a user via graphical user interface (GUI), are known in the prior art. In particular, automated, cloud-based systems enabling an end-user (e.g. an end-user being a consumer or an employee of a business as an insurance or distribution company (e.g. broker)) to compose automatically a first-tier (insurance) and/or second-tier (re-insurance) risk-transfer product, after conducting a dialogue with a knowledge-based system, are known. Such systems reduce the dependences of first-insurers or reinsurers on both their information technology (IT) and their human experts, as e.g. actuarial experts. Such systems are able to adjust the dialogue interactively according to the specific needs of the users and ask for the relevant data needed for the desired risk-transfer product. However, vendor-specific digital retail stores for providing automated or semi-automated risk-transfer do not allow to aggregate, compare and monitor products from a wide array of provider systems as e.g. carrier or broker units. Further, selection is usually narrow, and availability is low.

There are different categories of digital risk-transfer platforms, in particular so called digital active and passive risk-transfer management platforms and digital marketplaces, which intend to provide aggregating digital available products from a wider array of providers. There, selection is technically wider, and availability is higher than in vendor-specific digital retail stores. A digital marketplace is a type of electronic platform where product or service information is provided by multiple third parties. Online marketplaces are the primary type of multichannel electronic commerce and can be a way to streamline the automated production process. In a digital marketplace, user transactions (i.e. interaction between carrier/broker and carrier/broker in B2B interaction (insurer/distributor driven) or interaction between carrier/broker and consumer in B2C interaction) are automatically processed by the digital marketplace platform and then made accessible to and completed by the participating retailer or wholesaler systems. These type of digital systems allow user systems to register, e.g. as client systems, thereby linking and transacting single items to many items e.g. for a "post-selling" fee. Some of the prior art digital marketplaces provide automated business-to-business (B2B) trading. Such examples of digital platforms that enabled electronic commerce between clients include e.g. VerticalNet, Commerce One, Covisint, or Aladdin by Blackrock. Other B2B online marketplaces focus on a limited range of digital service, such as EC21, Elance and eBay, and have not achieved the dominance digital marketplaces have obtained in B2C retail. B2B purchasing requires that digital marketplaces facilitate and automate complex digital transactions, such as a request for quotation (RFQ), a request for information (RFI) or request for proposal (RFP). Digital marketplaces belong to the technical field of information technology acting as digital intermediaries by connecting buyer systems and seller systems. There are digital marketplaces for the online outsourcing of services like IT services, search engine optimization, marketing, and skilled crafts and trades work. Microlabor digital marketplaces such as Upwork and Amazon Mechanical Turk allow freelancers to perform tasks which only require a client device, e.g. a computer device, and internet access, i.e. access to the world-wide backbone network. For example, Amazon's Mechanical Turk digital marketplace focuses on "human intelligence tasks" that are difficult to automate computationally and/or by other technical means. This includes so called content labelling and content moderation.

Typically, for many types of risk-transfer, the structure of the risk-transfer concerned makes them suitable for automation with regard to the automated composition/configuration of the risk-transfer products, the so-called UnderWriting (UW). Most risk-transfers consist of a number of common basic parts and elements to configure. These parts and elements are herein referred as "structuring blocks" of the risk-transfer, i.e. the risk-transfer structure defining the characteristics of the risk-transfer. Different combinations of these structuring blocks lead to different risk-transfer products. For a human-machine interface (HMI) as e.g. Graphical User Interface (GUI), and for the corresponding necessary dialogue between the machine and the user, it should be possible to automatically compose risk-transfer products or structures out of a set of such structuring blocks. The "human" is the user of the automated system, i.e. an insured or an insurer depending if a first-tier (insurance product) or second-tier (reinsurance product) risk-transfer has to be configurated, while the "machine" refers to the automated system, as e.g. an automated web server or cloud-based system or digital system of a provider e.g. an insurer for first-tier risk-transfer products or a reinsurer for second-tier risk-transfer products. For example, using the parameterization of structuring blocks, typically a system comprising a limited amount of structuring blocks can be obtained for non-customized risk-transfer products. In an example of life risk transfer, applying domain knowledge of the actuary filed of the life risk-transfer structures (structure given by the insurance product parameters), the risk-transfer structure (defined by the policy parameters) comprises the steps of defining and transferring a monetary amount transfer (premium) either on basis of a regular monetary transfer or as transfer of a lump sum, the user (beneficiary) receiving an endowment if the insured is alive, which means that the insurer has to pay the beneficiary a sum of money (i.e. the benefit) in the case of death in exchange for the premium transfer. Depending on the risk-transfer parameters, other events such as terminal illness or critical illness can also trigger payment. Unseen the latter, the life risk-transfer can therefore be reduced to three basic event blocks. These events can be assigned to a set of structuring blocks common to all life risk-transfer: premium endowment and alive. For automation, all such systems depend on triggers. Triggers detect events in its environment by observing, measuring and/or monitoring properties or characteristics of input stimuli, as measuring parameters, it receives or measures. Finally, based on the used structuring blocks, the dialogue input flow of the user interface (HMI) may follow pairs of current state and input to what the present output and the next state must be. Thereby, the input triggers the next state.

Today, automation of the underwriting process is not enough to cope with the challenges. Risk-transfer, at the level of the first tier risk transfer (insurance) or second tier risk transfer can e.g. be broader supported by diversifying the risk shares of the risk transfer. However, quantifying and optimizing the risk measure by varying the risk shares is not a part of normal UW processes. Further, the increasingly dynamic and diversified (re)insurance market requires shorter time-to-market of highly customized (re)insurance products. Such process are technically difficult to automatize. Though prior art systems are able to automate or semi-automate the underwriting process, there is still a need for more completely automated electronic solutions covering the whole risk-transfer. In particular, there is no system providing a fast, consistent and easy access to reinsurance risk-transfer, thereby allowing to reduce administration costs for managing risk portfolios, (ii) to access fast, automatic capacity approval for medium-sized single risks or facilities, and (iii) to relieve administration time, to focus on more complex parts of the risk-transfer. In summary, there is a need for more efficient digital risk placement, claim handling and accounting channels for users covering possibly the whole process of the risk-transfer, i.e. the entire value chain providing an end-to-end process, thereby providing fast composing, launch and configuration of highly customizable (re) insurance products.

Another subject is operational stability and endurance of risk-transfer system in the varying external condition of the market. Conventionally, there are different broad technical categories of automated risk-transfer portfolio management systems. As mentioned, one prior art risk-transfer portfolio management system category is based on active management, wherein the risk-transfers are selected by the system for a portfolio individually based on measures quantifying impacting economic, financial, credit, and/or business parameters, based on technical trends, based on cyclical patterns etc. Another conventional category is passive management systems, also called indexing, wherein the risk-transfers in a portfolio duplicate those that are triggered by an index measure. The risk-transfers, in a passively managed portfolio, are weighted by relative market weighting or equal weighting (e.g. based on capitalization parameters). Another middle ground conventional category of risk-transfer portfolio management systems are called enhanced indexing systems, in which a portfolio's characteristics, performance and holdings are substantially dominated by the characteristics, performance and holdings of the index measure, albeit with modest active management departures from the index measure. The risk-transfer or (re)insurance marketplace consists of numerous products that have evolved out of the most basic designations of risk exposure and accumulation of risk balancing resources. Methodologies for scoring and rating the products that are associated with differences given by the operational parameters can result in real price and term discontinuities. As known, it is possible through one kind of risk-transfer product engineering to change high risk-transfer portfolios into lower risk ones through various kinds of aggregation, diversification, hedging and division of risk. As a result, a single C risk can be reconfigured into a product that appears to have AAA-risk characteristics. Of course, the individual risk-transfer product retains the same characteristic that it always had; it is the pooled, reconfigured and reengineered aggregation of the risk-transfers that is measured differently. The difference is most easily seen as the portfolio becomes increasingly granular. The disease in the form of a potentially toxic alignment of risk elements that might occur in either a singular or complex alignment of risks that might infect one class or sub-class of risk-transfer products may not necessarily spread to the whole portfolio or it, in contrast, generate a systemic risk. Risk, as used herein, is defined as a technical term, i.e. as a measurable probability measure for an occurrence or a plurality of occurrences of a defined, physical event having a measurable impact on a risk-exposed object or individual, wherein the risk measure relates to a predefined time-window (present of future) and geographic location.

A measurable quantity of the stability and endurance of an automated system, i.e. an automated (re)insurance unit, can be provided by a quantified resilience measure. Resilience is a measure for the operational stability and ability of staying power of a system through changing market parameters, market peaks and valleys, across established and emerging markets, and spanning decades of years in the market. It is also measure for the system's ability to attract new customers, and keep customers loyal to the use of the system in the market. It is to be noted, that for the measured quantity of the present invention, the measured resilience score is defined as introduced below.

Finally, a further disadvantage of the known prior art digital platforms and marketplaces is that those automated structures are not enabled to build up a complete automation technology providing a digital environment for supplier systems, e.g. insurer units, broker units, agent units etc. and consumer units, e.g. insured, where all units are able to participate in automated, digital processed transactions and risk-transfers covering B2B (Business to Business) as well as B2C (Business to Consumer) structures. B2B and B2C structures are based on two very different models, requiring for automation different skills, disciplines and mind-sets. In the prior art, the systems typically try to avoid running with both without splitting the system. B2C is where there is a buyer unit and a seller unit and they interact electronically at the digital platform as a point of sale or point of transaction. The point of sale could be realized as a digital marketplace or cloud-based platform. At the point of sale, the technical system provides an interaction between the units. In B2B there is no structure which can be denoted as a "point of sale". In digital systems based on B2B interaction, there is a relationship or linkage. Typically, it is a somehow developing or evolving relationship. Thus, a point of sale is B2C and a long-term relationship or linkage is B2B, both having different technical issues such as the automation of the Key Account Management and Customer-Relationship-Management CRM (B2B), and the automation of the Net Promoter Score and Customer-Experience-Management CXM (B2C) become easier to understand. For example, customer satisfaction surveys can be a solution for B2B relationship audits, but are inappropriate for B2C, since the essence of B2B are strong relationships, solutions to problems joint-ventures designing new warehouses, joint development and testing of new products. In the example of insurance systems, most insurance system activity can be classed as B2C, including risk-transfers for motor, house and small business units. However, property developers, ship owners and big businesses have specialist needs and typically will involve human experts as risk managers to liaise with their insurance companies in order to keep the risk-transfer cover and the risk exposure at appropriate levels at all times. This is where B2B structures provide appropriate relationships. Insurance systems will have dedicated units to look after these customers. In other words, the B2C relationship between customer, broker and insurer is linear whereas the specialist B2B relationship between customer, broker and insurer is triangular or circular.

Concerning the automation of digital platforms and digital driven marketplace platforms, machines and automated agents are increasingly involved in digital market activities, including for data collection and measuring, forecasting, planning, transaction execution, and other activities. This includes increasingly high-performance systems, such as used in high-speed trading. A need exists for methods and systems that improve the machines that enable markets, including for increased efficiency, speed, reliability, and the like for participants in such markets. Many digital marketplace platforms are increasingly distributed, rather than centralized, with distributed ledgers like Blockchain, peer-to-peer interaction models, and micro-transactions replacing or complementing traditional models that involve centralized authorities or intermediaries. A need exists for improved machines that enable distributed transactions to occur at scale among large numbers of participants, including human participants and automated agents. Operations on blockchains, such as ones using cryptocurrency, increasingly require energy-intensive computing operations, such as calculating very large hash functions on growing chains of blocks. Systems using proof-of-work, proof-of-stake, and the like have led to "mining" operations by which computer processing power is applied at a large scale in order to perform calculations that support collective trust in transactions that are recorded in blockchains. Many applications of artificial intelligence also require energy-intensive computing operations, such as where very large neural networks, with very large numbers of interconnections, perform operations on large numbers of inputs to produce one or more outputs, such as a prediction, classification, optimization, control output, or the like. A major challenge for human life risks and asset owners' risk and carriers of risk-transfer is the uncertainty involved in optimizing a living object or asset in respect to its measured risk exposure, or also associated risks such as resulting from volatility in the cost and availability of improvements (in particular where less stable renewable resources are involved), variability in the cost and availability of resources, and volatility and uncertainty in various end markets to which risk-improving or risk-protecting resources can be applied, among other factors.

SUMMARY OF THE INVENTION

It is an object of the invention to provide a digital marketplace platform, operatable in both fields of L&H and P&C, thereby providing automated risk assessment and risk-transfer (including UW and claim handling), by covering the whole process and providing a fully automated consumer (B2C) and insurer/carrier (B2B) marketplace platform, wherein the performance and the risk-transfer products/portfolios should be ratable by an appropriate quantified measure, in particular by rating/measuring quantitatively the potential risk (frequency and severity) of risk-transfer products/portfolios. The system should allow for systematic capturing, measuring, quantifying, and forward-looking generating of appropriate risk and risk accumulation measures of risk-transfers and risk-transfer portfolios associated with risk exposures of living objects (humans) (L&H) and physical real-world assets (P&C) based on physical measuring parameter values and data, i.e. the impact of a possibly occurring physical event in a defined future time window. In the present invention, this includes measuring and calculating the risk score ("personal resilience score" for L&H) of the life or health of a person or various P&C risk of an asset. It is a further object of the present invention to propose a processor-driven system or platform providing an automated digital channel for automatically concluding and dynamically adapting risk-transfers between a risk-transfer service user and a risk-transfer service provider, which does not exhibit the disadvantages of the known systems. In particular, it is an object of the present invention to propose a processor-driven, metric system or digital platform which comprises a user interface, which can be operated by means of terminals via a data-transmission network for users, comprising data input fields for inputting data relating to the object of a risk-transfer, which is available and can be used as a one-stop, end-to-end process for conducting, monitoring and adapting risk-transfers or portfolios of risk-transfers by the user. In particular, it is a further object of the present invention to propose a processor-driven, computer-based system which comprises a universal user interface which can be adapted flexibly to variable risk-transfer conditions and risk-transfer types of an automated binding process. The used inventive technical teaching should be easily integratable in other processes, productions chains or risk assessment and measuring systems, e.g. by appropriate APIs.

According to the present invention, these objects are achieved particularly through the features of the independent claims. In addition, further advantageous embodiments follow from the dependent claims and the description.

According to the present invention, the above-mentioned objects are particularly achieved by the inventive, automated, digital, cloud-based marketplace platform providing fully automated, end-to-end risk-assessment and risk-transfer processes by configuring, launching and processing of customized first-tier and/or second-tier risk-transfer products for risk-exposed consumers (comprising the exposure of L&H risks and P&C risks (i.e. the consumer for P&C risks is the owner of the asset) as first units and carriers/brokers as second units, wherein an automated risk-transfer placement is provided by the digital platform in a digital environment by a first online channel comprising a parameter-driven, rule-based underwriting process for creating or participating at risk-transfer structures by means of a pricing and underwriting engine, wherein an automated claim handling is provided by the system by means of a claim triage and handling engine as a second online channel, and wherein an automated accounting is provided by the platform by a balance sheet provision and management engine and policy administration engine as a third online channel, in that the digital platform comprises means for rating each first unit and each digital service of the platform by a contribution measure to a resilience score of the first units purchasing the risk-transfer products on the digital marketplace platform and benefiting from the digital services of the digital platform, in that the resilience score provides a measure based on the measured current health status of the first unit and/or the measured probability to purchase risk-transfer cover and/or the measured probability to start or keep behavior for improving their health status (In the sense of the present invention, this explicitly comprises the dynamic ups and downs of the health status itself, thus dynamically impacting the measured risk assessment provided by the digital platform. The present invention is able to cover the dynamic nature of risk-transfer products that managed through and interacted by the marketplace platform), in that the measuring of the resilience score encompasses different type of risks at least comprising mortality risks and/or morbidity risks and/or longevity risks together with the probability to claim for a risk-transfer benefit and/or the measured evolving health status of the first unit, and in that the contribution measure to the resilience score is measured by assessing the variance of a first unit's resilience score by changing first unit's parameter at least comprising adding or omitting a specific risk-transfer cover and/or triggering start or maintenance of a nutrition program. It is important to note, that the processing of the digital platform is not limited to nutrition programs. Nutrition is just an example of more generic approaches and programs, as complex "health/asset improvement/maintenance programs" (possibly for both human lives for L&H and/or physical assets for P&C).

The invention has inter alia the advantage that it provides an automated electronic digital channel to place and manage risks and risk-transfers between first risk-transfer systems or insurers and second risk-transfer systems reinsurers, in particular a digital B2B and B2C channel. The invention provides the technical infrastructure as a digital marketplace for an automated one-stop system comprising automated underwriting and user-specific data capturing, automated claim handling, automated accounting (technical and financial) and automated reporting all in one technical system and a based on the same resilience score as risk-transfer quality indicator. The system is able to provide automated risk-transfer coverage for all risk-specific fields as e.g. property and casualty risks, life and health risks, any line of business or industry risks, single risks, treaty and facility risks, and accumulation or clash risk involving loss exposure of one event spreading to multiple lines of business, i.e. correlated risk structures. The inventive system allows in a new technical way a user to monitor and fully control his risks along the entire value chain at any time. By the inventive resilience score, the invention provides a new kind of direct and full control and transparency of the risk-transfer portfolio to the user, in particular the invention provides early recognition of trends and agile risk-transfer steering by means of forward- and backward-looking metrics and measure values. The invention also provides technical means and API's which can be seamless integration with other technical solutions and systems as e.g. portfolio monitoring platforms. Thus, B2B and B2C users will have specific benefits for participating in the digital marketplace; for instance, (A) B2B benefits (for insurers and other distributors) are (i) access to consumer pool that is cheaper (streamline costs e.g., reducing acquisition costs for consumers on the marketplace, sharing back-office tools/processes, sharing legal checks/regulatory requirements) or broader (extend product offering; expand to new geographies; sell to individuals not traditionally interested in insurance, priced out or excluded) vs today), (ii) validated assessment of current status of resilience for each individual consumer; (iii) validated assessment of impact of services in the individual's resilience; and (iv) access to more and curated roster of service providers; and (B) B2C benefits (for consumers) are: (i) global portability of (resilience-relevant) data—e.g., data currently used to underwrite individuals; (ii) global portability of insurance coverage and/or service provision across geographies or providers; and (iii) security of individual data stored in a neutral platform vs each distributor.

BRIEF DESCRIPTION OF THE DRAWINGS

The present invention will be explained in more detail below relying on examples and with reference to these drawings in which.

DETAILED DESCRIPTION OF THE PREFERRED EMBODIMENTS

FIGS. 1 to 4 schematically illustrate an architecture for a possible implementation of an embodiment of the inventive digital system and platform 1 respectively digital platform for composing, launch and configuration of first and second-tier risk-transfer with built-in auditing and monitoring structures based on a resilience score measure. As mentioned above, resilience can be defined as a measurable quantity of the stability and endurance of a system, i.e. a (re)insurance unit. However, in the present invention the quantitative resilience score is provided as an outcome of the B2B/B2C users participating in the marketplace, where the resilience is a measure for the generic operational benefit. Thus, the term "resilience marketplace" is a digital marketplace that thanks to the interaction of B2B/B2C users and the services providers give at the digital market place, creates more "personal resilience" for the consumers that end up buying the insurance products.

Figure 1:
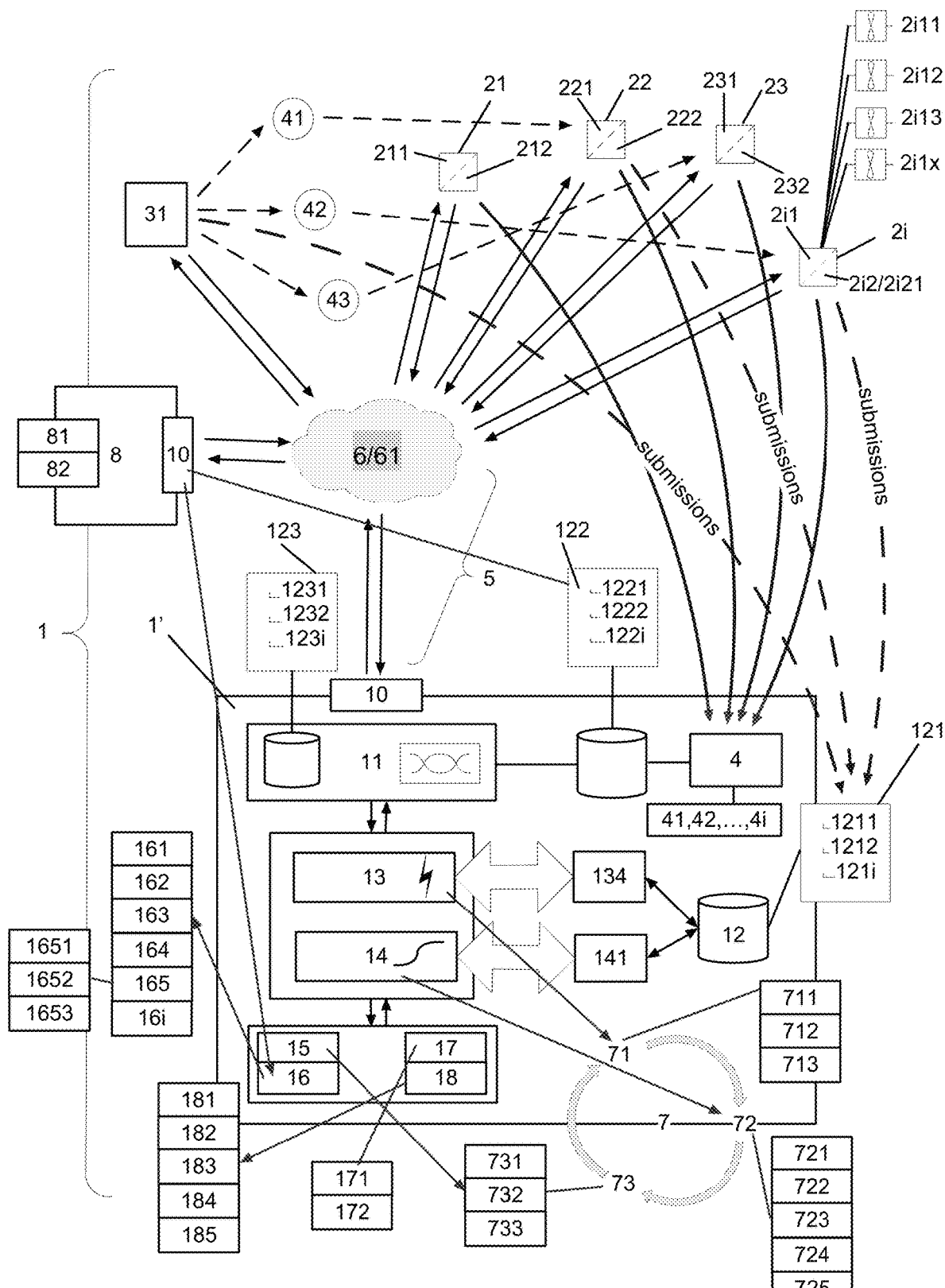
FIG. 1 shows a block diagram, schematically illustrating the automated end-to-end process according to the invention providing an efficient, automated online marketplace platform comprising underwriting, claims and accounting channels for users. The reference number 7 denotes the automated end-to-end process, 71 the automated underwriting process by means of a rule-based bifurcation process, 711 the creation of a submission, 712 the receiving and binding of a quotation, 713 the modifying and renewing of an acceptances, 72 the technical accounting process, 721 the booking of the premiums, 722 the advising on new claims, 723 the booking and updating of claims, 724 the rectifying of premiums, 725 the submission of a statement of accounts, 73 the financial accounting process, 731 the advising and/or requesting of payments, 732 the seamless pairing, and finally 733 the setting of the accounts. The proposed invention and method provides a fast and easy access to first and secondary risk-transfer underwriting, technical and financial accounting on a digital marketplace platform as digital environment. The invention allows to reduce technical and administrative input and costs for managing risk-transfer portfolios in the field of L&H and P&C risk assessment and risk-transfer (including UW and claim handling), covering the whole process by providing a fully automated consumer (and insurer/carrier) platform. A core feature is given by the platform by providing automated risk assessment in combination with the measured resilience score.
Figure 2:
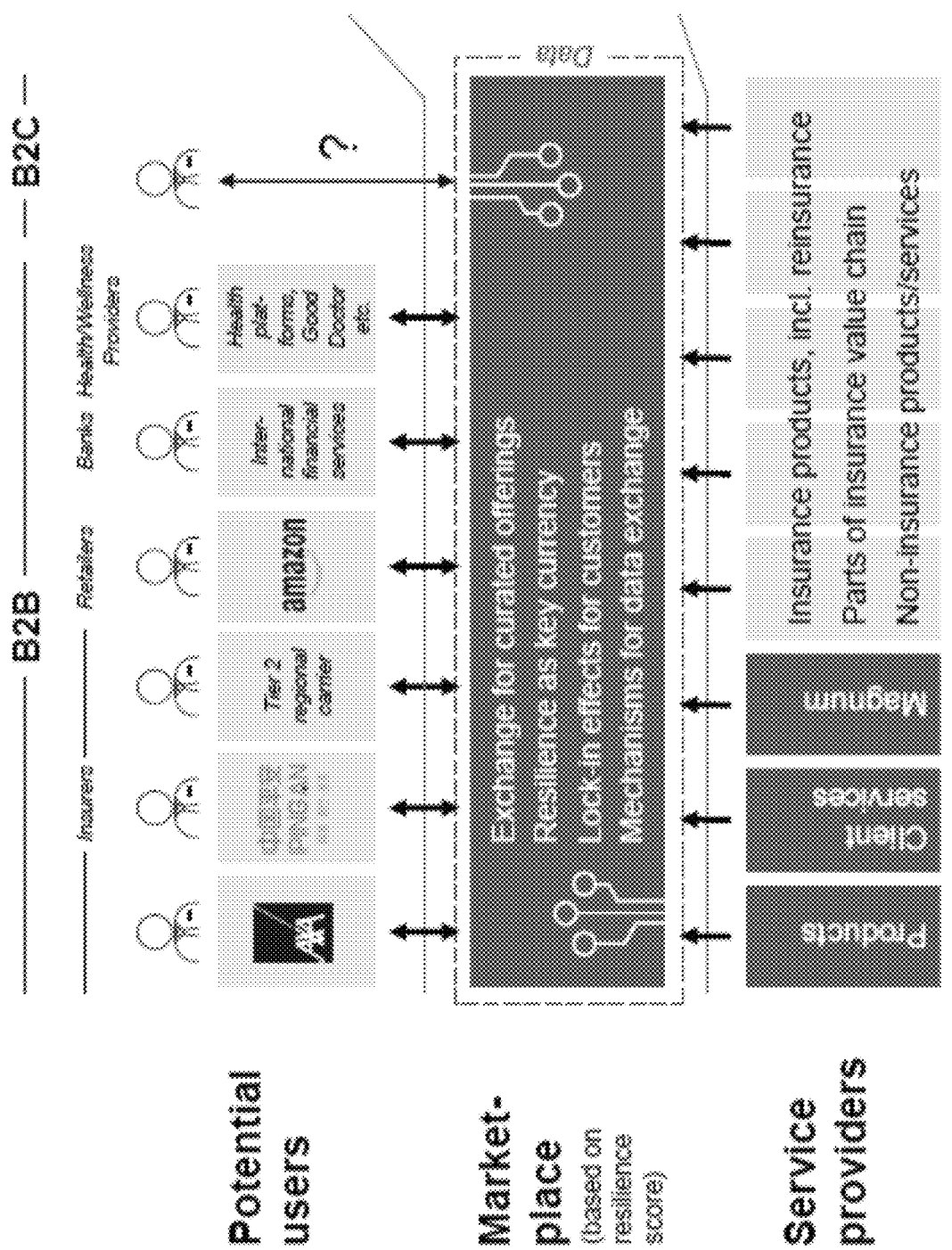
FIG. 2 shows a block diagram illustrating schematically an exemplary structure of the digital marketplace platform. As such, the digital platform is based on the use of digital platform technology and cloud-based technologies to provide a digital environment of supplier (here carriers such as AXA etc.) and consumers (insured) that participates in transactions, centralized analysis and exchanges.
Figure 3:
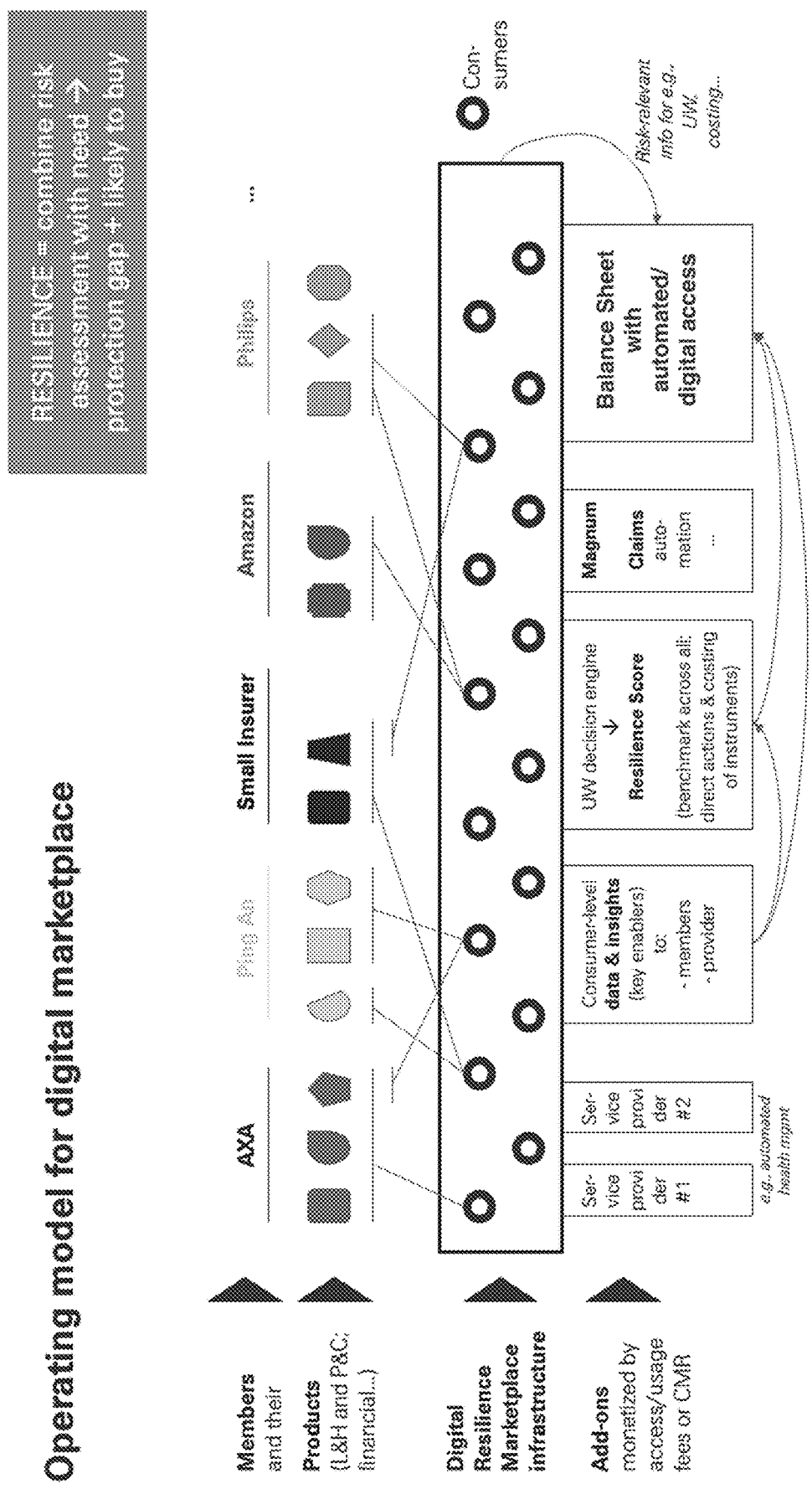
FIGS. 3 and 4 show a block diagram illustrating schematically an exemplary fully automated consumer (insured) and carrier/broker digital risk-transfer marketplace platform. The digital marketplace is centered on consumers and distributors along value chain. The platform dynamically provides offering that evolves with individual along lifecycle. The platform structure can be applied to any risks (LH/PC) and any channel (on/offline). The digital platform allows users to access and use the marketplace based on or without charging an appropriate fee. The platform enables and supports the users, aligning the users' interests to the extent possible, cutting out possible interference with users' decisions on product details, targeting, channels etc., underlying and/or commodity costs occur only once, and multiple, flexible add-ons are enabled. The digital platform enables full portability, i.e. consumer (first units) can "natively" move across providers, across geographies. It further provides and is based on a global personal Resilience Score measure, using multiple data sources. Each consumer's data is segregated and hold confidential and secure. Carriers can reinsure on reinsurer's balance sheet, however, don't have to. The platform provides further addons including: Access to (any) service provider via API, process automation for UW and claim handling, consumer advisory app, powered by the Resilience Score, and consumer-level insights, anonymized for benchmarking, pricing. The reference Magnum in the figures denotes a fully automated cloud-based digital solution for secure underwriting, individual risk assessment/measurement, and automated portfolio handling.
Figure 4:
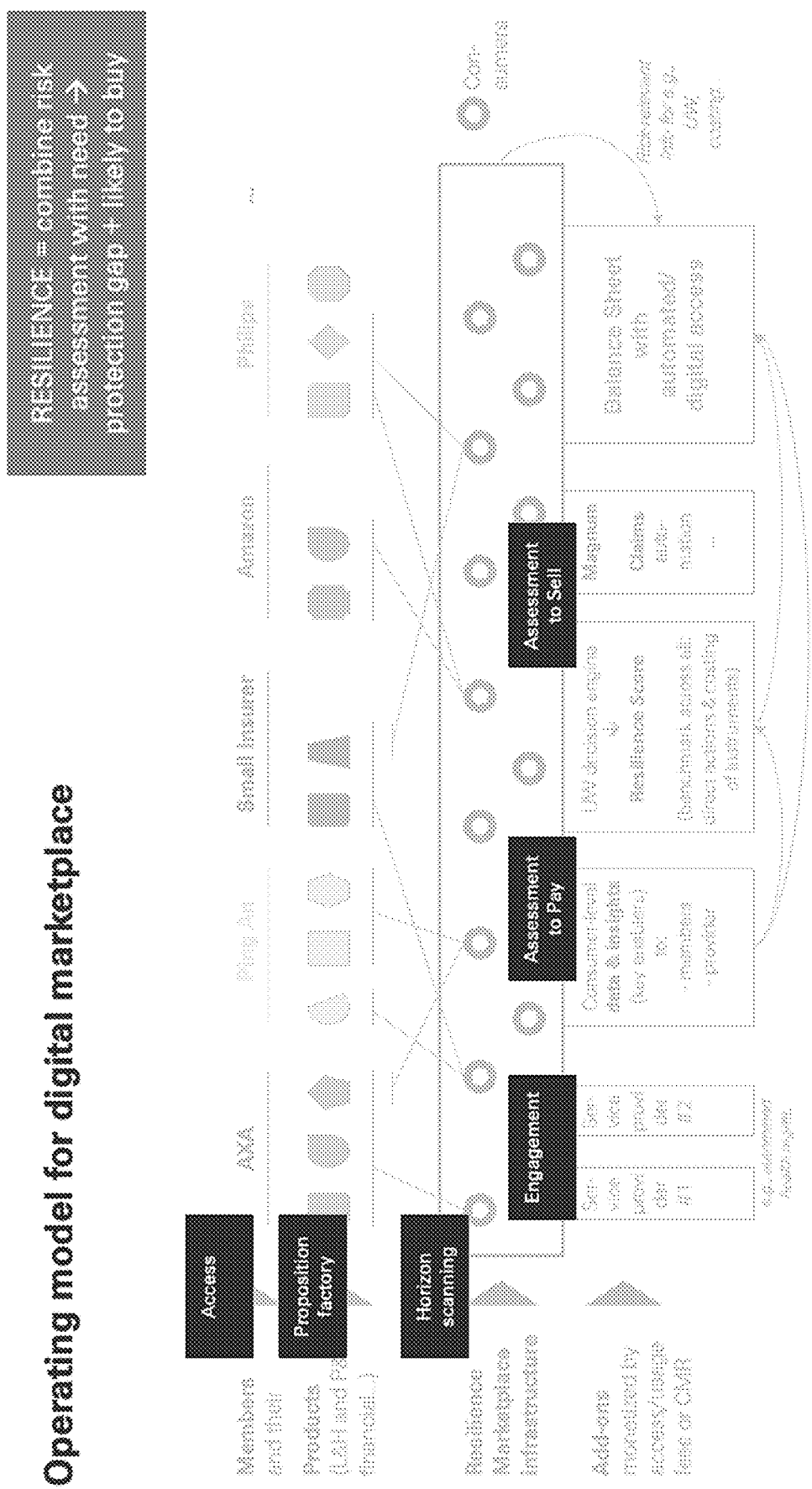

As FIG. 1 shows, the inventive, automated end-to-end process provides an efficient, automated online risk placement, claims and accounting channel for users with a complete electronic solution for automated business structuring. Thus, the invention provides, in the field of L&H and P&C risk-transfer, a digital marketplace platform with automated risk assessment and risk-transfer (including UW and claim handling), covering the whole process by providing a fully automated consumer (and insurer/carrier) platform. A key feature is given by the automated risk assessment in combination with the resilience score.

The digital platform 1 provides automated risk assessment in combination with the inventive resilience score, where the overall solution consists of curated offering for B2B and potentially B2C "users" or marketplace members: insurers, other distributors of insurance and other financial products, and direct consumers. Each will have a specific benefit for participating in the digital marketplace; for instance, (A) B2B benefits (for insurers and other distributors) are (i) access to consumer pool that is cheaper (streamline costs e.g., reducing acquisition costs for consumers on the marketplace, sharing back-office tools/processes, sharing legal checks/regulatory requirements) or broader (extend product offering; expand to new geographies; sell to individuals not traditionally interested in insurance, priced out or excluded) vs today), (ii) validated assessment of current status of resilience for each individual consumer; (iii) validated assessment of impact of services in the individual's resilience; and (iv) access to more and curated roster of service providers; and (B) B2C benefits (for consumers) are: (i) global portability of (resilience-relevant) data—e.g., data currently used to underwrite individuals; (ii) global portability of insurance coverage and/or service provision across geographies or providers; and (iii) security of individual data stored in a neutral platform vs each distributor.

In the digital marketplace platform 1, each individual and service provided on the digital marketplace is automatically rated on its contribution to a resilience measure of the consumers that purchase products on the digital marketplace and benefits from its services. The resilience score measure rates the current health status of individuals, and their likelihood to purchase insurance protection or start/keep behaviors that improve their health status. Current means that it can dynamically change (and be reassessed and recalculated) over the duration of the policy, i.e. the term of the risk-transfer, due to changes in health status, behaviors, illnesses . . . .

As such, the digital, cloud-based marketplace platform 1 provides fully automated, end-to-end risk-assessment and risk-transfer processes by configuring, launching and processing of customized first-tier and/or second-tier risk-transfer products 4/41, 42, . . . , 4i for risk-exposed consumers as first units 2 and carriers/brokers as second units 3. An automated risk-transfer placement 7 is provided by the digital platform 1 in a digital environment by a first online channel comprising a parameter-driven, rule-based underwriting process 71 for creating or participating at risk-transfer structures by means of a pricing and underwriting engine 13. An automated claim handling 72 is provided by the system 1 by means of a claim triage and handling engine 14 as a second online channel, and an automated accounting 73 is provided by the platform 1 by a balance sheet provision and management engine and policy administration engine 15 as a third online channel. The digital platform 1 comprises a rating engine 16 for rating each first unit 2 and each digital service 181, 182, . . . , 18i of the platform 1, e.g. provided by the monitoring and surveillance unit 18, by a contribution measure to a resilience score 161 of the first units 2 purchasing the risk-transfer products 4/41, . . . , 4i on the digital marketplace platform 1 and benefiting from the digital services 181, 182, . . . , 18i of the digital platform 1. The resilience score 161 provides a measure based on the measured current health status 162 of the first unit 2 and/or the measured probability to purchase risk-transfer cover 163 and/or the measured probability to start or keep behavior for improving their health status 164. The measuring of the resilience score 161 encompasses different type of risks at least comprising mortality risks 1651 and/or morbidity risks 1652 and/or longevity risks 1653 together with the probability to claim for a risk-transfer benefit (166) and/or the measured evolving health status 162 of the first unit 2. Finally, the contribution measure to the resilience score 161 is measured by assessing the variance of a first unit's resilience score 161 by changing first unit's parameter at least comprising adding or omitting a specific risk-transfer cover and/or triggering start or maintenance of a nutrition program.

Detected changes in the resilience score can e.g. trigger changes in pricing parameters and/or benefit parameters of one or more risk-transfer or financial products. The digital marketplace platform 1 can e.g. comprises standardized and dedicated interfaces for registering and/or authentication and/or authorization of new or existing first or second units. The digital marketplace platform 1 can e.g. comprise standardized and dedicated interfaces for the integration of new second units as service providers on the digital marketplace platform 1. The digital marketplace platform 1 can also comprise standardized and dedicated application programming interface (API) for data exchange and transfer between the digital marketplace platform 1 and a second unit.

As an embodiment variant, the digital marketplace platform 1 can e.g. comprises dedicated electronic links to external digital insurance engine and/or automated underwriting capabilities and/or claim automation means. The digital marketplace platform 1 can comprise interfaces providing access to electronic, second tier (reinsurance) balance sheets. The electronic balance sheet can e.g. be a life and health risk-transfer balance sheet or a property and casualty risk-transfer balance sheet.

The digital services of the marketplace platform 1 comprise B2B for second units and/or B2C digital services between first and second units:

The B2B digital services for second units at least can e.g. comprise an automated pricing and underwriting process by means of a pricing/underwriting engine. The B2B digital services can at least comprise an automated balance sheet provision and management engine providing automated accounting for second units, wherein a provision is represented by a digital account recording liabilities of a second unit arising from conducted risk-transfers, and wherein measurement of the amount assessed as provision is realized by best estimate of the expenditure required to settle the current detected obligation at a balance sheet date. The recording of the liability in a second unit's balance sheet can e.g. automatically matched to an assigned expense account. The B2B digital services at least can comprise an automated claim triage process and claim handling process processed by means of a claims triage and handling engine for second units. The B2B digital services can at least comprise an automated policy administration process processed by means of a policy administration engine between second units. The B2C digital services can further at least comprise an automated engagement and sales process accessible via the digital marketplace platform or via a client application accessing the digital marketplace platform provided by an automated engagement and sales engine.

The B2C digital services can at least comprise an allocation of automatedly adapted generic or user-specific programs, as dynamically adapted "health improvement/behavioral changes" programs, such as nutrition program processes, by means of a program engine. The adaption comprises an automated, dynamic assessment and measurement of the changing risks under the program process by the digital platform 1'. The B2C digital services can at least comprise an allocation of automatedly adapted health and disease management program processes by a health and disease management engine. The B2C digital services can at least comprise monitoring means for monitoring a current resilience status based on the measured resilience score accessible via an advisory application of the digital platform. The advisory application can e.g. comprise an expert module providing expert advices and opportunities for improvement of the individual resilience score.

The contribution to resilience of each component of the marketplace services can e.g. be assessed individually by the digital marketplace platform. The digital platform can e.g. comprise means for selecting and/or rating of each first and/or second unit. The digital platform can e.g. further comprise rating means for measuring and ensuring quality assurance.

The digital platform 1 can e.g. comprise means for assessing risk parameters capturing risk-exposure of first units as risk-exposed consumers (the term "consumers" denoting both individuals exposed to L&H risks and owners of risk-exposed assets (P&C risks)), wherein the digital platform comprises a product configurator with a machine-based exposure data intelligence enabled to automatically identify risks of first units based on the captured risk-parameters of the first unit. The digital platform 1 can comprise a metric simulation engine for automated prediction of forward- and backward-looking impact measures based on risk-event parameter values of time-dependent series of occurrences of physically impacting risk-events, wherein the occurrences of the physical risk-events are measured based on predefined threshold-values of the event parameters and wherein the impacts of the risk-events to a specific first unit are measured based on impact parameters associated with the first unit. Finally, the digital platform 1 can e.g. comprise a graphical user interface of a portfolio analytics framework providing a dynamic representation of a portfolio structure, wherein a metric simulation engine forms an integrated part of the portfolio analytics framework, and wherein, by means of the metric simulation engine, the dynamic representation of the portfolio structure provides forward- and backward-looking insights to the user based on the measured resilience score thereby enabling portfolio steering by identification of critical areas of the portfolio and impacts of possible changes to the underwriting.

The digital platform and system 1 provides an automated, multi-channel, end-to-end risk-transfer product configuration process 2 for configuring, launching and processing of first and/or second-tier risk-transfer structures. Thus, the digital platform and automated risk-transfer configurator allows fast composing, launching and configuration of customized first and/or secondary risk-transfer structures. An automated risk-transfer product placement is provided by the platform 1 as a first online channel comprising a parameter-driven, rule-based underwriting process 71 for creating a portfolio of customized second-tier structures. An automated claim handling 72 is provided by the platform 1 as a second online channel, and an automated accounting 73 is provided by the system 1 as a third online channel. The platform 1 comprises a product configurator for providing the automated underwriting by means of a rule-based bifurcation process 71. The product configurator comprises at least four structuring blocks, a first structuring block for setting coverage parameters of the risk-transfer product, a second structuring block for setting line of business parameters, a third structuring block for setting type of risk-transfer parameters, and a fourth structuring block for setting risk parameters. For capturing the risk parameters the product configurator can e.g. comprise a machine-based exposure data intelligence enabled to automatically identify unique risks of objects. The system further comprises the metric simulation engine for automated prediction of forward- and backward-looking impact measures based on event parameter values of time-dependent series of occurrences of physical impacting risk-events. The occurrences of the physical risk-events are measured based on predefined threshold-values of the event parameters and the impacts of the physical risk-events to a specific asset or object are measured based on impact parameters associated with the living object (human) or asset. The platform 1 comprises a graphical user interface of a portfolio analytics framework providing a dynamic representation of the portfolio structure, wherein the metric simulation engine forms an integrated part of the portfolio analytics framework. By means of the metric simulation engine, the dynamic representation of the portfolio structure provides forward- and backward-looking insights to the user based on the resilience score measure thereby enabling portfolio steering by identification of critical areas of the portfolio and impacts of possible changes to the underwriting.

As a variant, the digital, cloud-based marketplace platform 1 comprises a controller, comprising a living object or asset model circuit structured to operate a digital twin for living object or asset associated with first units 2, and sensory and measuring devices 2i11-2i1x of the digital platform 1 measuring and capturing of measuring data 1221, . . . , 122i measuring risk-exposer and characteristics of consumer unit 2i by means of the sensory and measuring devices associated with the unit 2, and a living object or asset description circuit structured to interpret the measured measuring parameters 1221, . . . , 122i from the digital twin for the living object or asset, and a living object or asset configuration circuit structured to operate an adaptive learning system, wherein the adaptive learning system is configured to dynamically adjust a living object or asset configuration based on the set of measuring parameters 1221, . . . , 122i from the digital twin based at least in part on risk-relevant characteristics. The adaptive learning system can e.g. comprise at least one of a machine learning system and an artificial intelligence (AI) system. In the digital platform 1, adjusting the living object or asset configuration can further comprise performing a submission transaction for creating or participating at risk-transfer structures and/or corresponding purchase or sale transactions on the digital marketplace platform 1. The digital platform 1 can e.g. comprises forecasting means 16 for an additional forward-looking rating of each first unit 2 and each digital service 181, 182, . . . , 18i of the platform 1 by a contribution measure to a forecasted resilience score 161 of the first units 2 for a definable future time window for purchasing the risk-transfer products 4/41, . . . , 4i on the digital marketplace platform 1 and benefiting from the digital services 181, 182, . . . , 18i of the digital platform 1. The living object configuration circuit can e.g. be structured to adaptively improve one of a risk-exposure measure parameter of the living object or asset or a cost of operation of the living object or asset for improving its measured risk exposure or for using executed transactions on the digital, cloud-based marketplace platform 1. The measured risk-exposure can e.g. be further associated with a digital platform task. The digital platform 1 can e.g. comprise means for dynamically adjusting the living object or asset configuration further comprises measuring the performing transaction-enabling submissions by the unit 2 on the digital marketplace platform. The living object or asset description circuit can further be structured to interpret detected and measured conditions based on the measuring parameters 1221, . . . , 122i, wherein the detected conditions comprise at least one condition selected from the conditions consisting of: an input resource for the living object or asset; a living object or asset resource; an output parameter for the living object or asset; or an external condition related to the living object or asset; and wherein the living object or asset model circuit is further structured to dynamically and/or in real-time update the digital twin for the living object or asset in response to the detected conditions. The measuring parameters 1221, . . . , 122i can e.g. comprise at least partly telematic measuring parameters measured by telematic measuring devices 2i11-2i1x of the digital platform 1 associated with first units 2.

The measuring parameters 1221, . . . , 122i, in particular the telematics measuring parameters 1221, . . . , 122i are nothing but the parameters obtained from one or several parts of the living object or asset of the unit 2 during its operation/living term such as, temperature in radiator, viscosity of the engine oil and force applied over the brake disk, health parameters blood pressure, heartbeat rate, body fat parameters, blood sugar etc. These measuring parameters 1221, . . . , 122i a are gathered using several sensors implanted in or attached to different parts of an asset or a living object and are continuously transmitted to backend capturing means of the digital platform 1 to develop the digital twin structure associated with the living object or asset, which is a virtual model of the physical living object or asset. Later, measured measuring parameters 1221, . . . , 122i are analyzed by the digital platform 1 using data mining algorithms to predict the failures or occurring risks or risk developments or resilience score measure developments assigned with an asset or a living object well in advance, better insights into performance and condition of an living object or asset thereby recommending alternative management of risks as an automated expert system. The digital platform 1 comprises the above-discussed means for the creation of digital twin using e.g. using Eclipse Hono, Eclipse Kura and Eclipse Ditto. Further, measuring parameters 1221, . . . , 122i gathering and processing at the digital platform 1 can also be performed remote. The prediction can be performed using e.g. Turbofan Engine Degradation Simulation Dataset by means of several machine learning regression algorithms and compare their accuracies. It has to be mentioned that typically Gradient Boost Regressor provides better accuracy in the predicting future measures e.g. of a future resilience score measure, or risk exposure measures associated with the corresponding living object or asset.

| List of reference signs |
|---|
| 1 Digital Marketplace |
| 1' Digital Marketplace Platform |
| 10 Secure Data Transmission Network Interface |
| 11 Marketplace Module |
| 12 Persistent Storage |
| 121 Data Segment comprising risk-transfer data elements 121i |
| 1211, 1212, . . . , 121i Digital risk-transfer Data Element |
| 122 Data Segment comprising consumer data elements 122i |
| 1221, 1222, . . . , 122i Digital Consumer Data Element |
| 123 Data Segment comprising carrier/broker data elements 123i |
| 1231, 1232, . . . , 123i Digital Carrier/Broker Data Element |
| 13 Pricing and underwriting engine |
| 14 Claim triage and handling engine |
| 15 Accounting module/Balance sheet provision and management/Policy administration engine |
| 16 Resilience Score Rating Module |
| 161 Resilience score |
| 162 Health status (current/evolving) |
| 163 Probability to purchase risk-transfer cover |
| 164 Probability to start or keep behavior for improving their health status |
| 165 Risks encompassed by the resilience score |
| 1651 Mortality risks |
| 1652 Morbidity risks |
| 1653 Longevity risks |
| 166 Probability to claim for a risk-transfer benefit |
| 17 Web Server/Network Server |
| 171 Firewall |
| 172 Router |
| 18 Monitoring and surveillance unit |
| 181 Monitoring of the contribution to resilience of each component of the marketplace services |
| 182 Selection/rating of each provider monitoring |
| 183 Quality assurance monitoring |
| 184 Risk engineering parameter monitoring |
| 185 Expert system advising with knowledge and parameters insights |
| 2 Consumer units (first units) |
| 21 Consumer Unit ($C_{21}$) associated with consumer unit data element 1221 |
| 22 Consumer Unit ($C_{22}$) associated with consumer unit data element 1222 |
| . . . |
| 2i Consumer Unit ($C_{2i}$) associated with digital consumer unit data element 122i |
| 2i11-2i1x Sensory and measuring devices of the digital platform 1 measuring and capturing of measuring data measuring risk-exposer and characteristics of consumer unit 2i by means of the sensory and measuring devices associated with the unit 2 |

-continued

List of reference signs

3 Carrier/broker units (second units)
31 Carrier/Broker Unit ($B_{21}$) associated with carrier/broker unit data element 1231
32 Carrier/Broker Unit ($B_{22}$) associated with carrier/broker unit data element 1232
...
3i Carrier/Broker Unit ($B_{2i}$) associated with carrier/broker unit data element 123i
4 Risk-transfers
41 Risk-transfer ($R_{41}$) associated with the risk-transfer data element 1211
42 Risk-transfer ($R_{42}$) associated with risk-transfer data element 1212
...
4i Risk-transfer ($R_{4i}$) associated with risk-transfer data element 121i
5 Secured Network and Network Accesses to digital marketplace platform
6 Data transmission Network
61 Internet, Worldwide Backbone Network
7 Processes
71 Automated parameter-driven, rule-based underwriting process
771 Rule-based bifurcation process
772 Receiving and binding of a quotation
773 Modifying and renewing of an acceptances
72 Automated claim handling processes
721 Booking of premiums
722 Advising on new claims
723 Booking and updating of claims
724 Rectifying of premiums
725 Submission of a statement of accounts
73 Automated accounting processes
731 Advising and/or requesting of payments
732 Seamless pairing
733 Setting of the accounts
8 3rd-party service provider units providing services as (i) health management/behavior programs (nutrition etc.) and/or (ii) other risk scoring/risk assessment (e.g. credit scoring). Units 8 are connected to the consumer data 122 but sit outside the digital market place 1' and can provide additional inputs to the resilience score rating module 16.
81 Health management/behavior programs (nutrition etc.)
82 Other risk scoring/risk assessment (e.g. credit scoring)

The invention claimed is:

1. A system that implements a digital, cloud-based marketplace platform, the system comprising:
processing circuitry;
a metric simulation engine; and
a graphical user interface,
the digital platform enabling fully automated, end-to-end risk-assessment and risk-transfer processes by configuring, launching and processing of customized first-tier and/or second-tier risk-transfer products for risk-exposed consumers as first units and carriers/brokers as second units, wherein
the risk-transfer products consist of a number of structuring blocks being common basic parts and elements to configure the risk-transfer products,
different combinations of the structuring blocks provide different risk-transfer structures which define characteristics of the risk-transfer products,
an automated risk-transfer placement is provided by the digital platform in a digital environment by a first online channel comprising a parameter-driven, rule-based underwriting process for creating or participating at risk-transfer structures by a pricing and underwriting engine,
an automated claim handling is provided by the digital platform by a claim triage and handling engine as a second online channel, and
an automated accounting is provided by the digital platform by a balance sheet provision and management engine and policy administration engine as a third online channel,
the processing circuitry being configured to rate each first unit and each digital service of the digital platform by a contribution measure to a resilience score of the first units purchasing the risk-transfer products on the digital platform and benefiting from the digital services of the digital platform, the resilience score providing a measure based on a measured current health status of each first unit and/or a measured probability to purchase risk-transfer cover and/or a measured probability to start or keep behavior for improving health status, wherein measuring of the resilience score encompasses different type of risks at least comprising mortality risks and/or morbidity risks and/or longevity risks together with probability to claim for a risk-transfer benefit and/or measured evolving health status of each first unit,
the processing circuitry including;
a living object or asset model circuit configured to operate a digital twin for living object or asset associated with the first units,
sensory and measuring devices measuring and capturing of measuring data measuring risk-exposer and characteristics of a consumer unit by the sensory and measuring devices associated with a first unit,
a living object or asset description circuit configured to interpret the measured measuring parameters from the digital twin for the living object or asset, and
a living object or asset configuration circuit configured to operate an adaptive learning system, wherein the adaptive learning system is configured to dynamically adjust a living object or asset configuration based on a set of measuring parameters from the digital twin based at least in part on risk-relevant characteristics,
the processing circuitry being configured to perform a forward-looking rating of each first unit and each digital service of the digital platform by a contribution measure to a forecasted resilience score of the first units for a definable future time window for purchasing the risk-transfer products on the digital platform and benefiting from the digital services of the digital platform,
the processing circuitry being configured to measure the contribution measure to the resilience score by assessing variance of a resilience score of a first unit by changing a parameter of the first unit at least comprising adding or omitting a specific risk-transfer cover and/or triggering start or maintenance of a nutrition program,
the metric simulation engine being configured to automate prediction of forward- and backward-looking impact measures based on event parameter values of time-dependent series of occurrences of physically impacting risk-events, the occurrences of the physically impacting risk-events being measured based on predefined threshold-values of the event parameters and impacts of the physically impacting risk-events to the first unit being measured based on impact parameters associated with the first unit,
the processing circuitry being configured to perform an additional forward-looking rating of each first unit and each digital service of the digital platform by a contribution measure to a forecasted resilience score of the first units for a definable future time, and
the graphical user interface being of a portfolio analytics framework configured to provide a dynamic representation of a portfolio structure, the metric simulation engine forming an integrated part of the portfolio analytics framework, and, via the metric simulation engine, the dynamic representation of the portfolio structure provides forward- and backward-looking insights to the first unit based on the measured resilience score measure, enabling portfolio steering by identification of critical areas of the portfolio and impacts of possible changes, wherein detected changes in the resilience score triggers dynamic changes in pricing parameters of one or more risk-transfer.

2. The system according to claim 1, wherein dynamically detected changes in the resilience score trigger at least dynamic assessment and/or reassessment and/or repricing by the digital platform at inception and throughout a duration of a risk-transfer and/or of a user relationship established by the digital platform.

3. The system according to claim 1, wherein in case a user has multiple risk-transfer products with multiple carriers/brokers, the processing circuitry uses same inputs to update the resilience score of the user which is then fed back to all carriers/brokers for dynamic reassessment and/or repricing of their respective risk-transfer products.

4. The system according to claim 1, further comprising standardized and dedicated interfaces for registering and/or authentication and/or authorization of new or existing first or second units.

5. The system according to claim 1, further comprising standardized and dedicated interfaces for an integration of new second units as service providers on the digital platform.

6. The system according to claim 1, further comprising standardized and dedicated application programming interface (API) for data exchange and transfer between the digital platform and a second unit.

7. The system according to claim 1, further comprising dedicated electronic links to an external digital insurance engine and/or automated underwriting capabilities and/or claim automation devices and/or external service providers of health or risk management program processes and/or automated risk assessments.

8. The system according to claim 7, wherein the automated risk assessments at least comprise automated credit scores and/or credit scoring.

9. The system according to claim 1, further comprising interfaces providing access to an electronic, second tier (reinsurance) balance sheet.

10. The system according to claim 9, wherein the electronic, second tier (reinsurance) balance sheet is a life and health risk-transfer balance sheet or a property and casualty risk-transfer balance sheet.

11. The system according to claim 1, wherein the digital services of the digital platform comprise B2B for the second units and/or B2C digital services between the first and second units and/or B2B or B2C between users of the digital platform and external service providers of health or risk management program processes and/or automated risk assessments.

12. The system according to claim 11, wherein the B2B digital services for the second units at least comprise an automated pricing and underwriting process by a pricing/underwriting engine.

13. The system according to claim 11, wherein
the B2B digital services at least comprise an automated balance sheet provision and management engine providing automated accounting for the second units, wherein a provision is represented by a digital account recording liabilities of a second unit arising from conducted risk-transfers, and
measurement of an amount assessed as provision is realized by best estimate of an expenditure required to settle a current detected obligation at a balance sheet date.

14. The system according to claim 13, wherein the recording of a liability in a balance sheet of the second unit is automatically matched to an assigned expense account.

15. The system according to claim 11, wherein the B2B digital services at least comprise an automated claim triage process and a claim handling process processed by a claims triage and handling engine for the second units.

16. The system according to claim 11, wherein the B2B digital services at least comprise an automated policy administration process processed by a policy administration engine between the second units.

17. The system according to claim 11, wherein the B2C digital services at least comprise an automated engagement and sales process accessible via the digital platform or via a client application accessing the digital platform provided by an automated engagement and sales engine.

18. The system according to claim 11, wherein the B2C digital services at least comprise an allocation of automatically adapted nutrition program processes by a nutrition program engine.

19. The system according to claim 11, wherein the B2C digital services at least comprise an allocation of automatically adapted health and disease management program processes by a health and disease management engine.

20. The system according to claim 11, wherein the B2C digital services at least comprise monitoring devices for monitoring a current resilience status based on the measured resilience score accessible via an advisory application of the digital platform.

21. The system according to claim 20, wherein the advisory application comprises an expert module providing expert advices and opportunities for improvement of individual resilience score.

22. The system according to claim 1, wherein the processing circuitry is configured to assess individually the contribution to resilience of each component of the digital services based on a consumer's health status and/or an asset's risk characteristics.

23. The system according to claim 1, wherein the processing circuitry is configured to select and/or rate each first and/or second unit.

24. The system according to claim 1, wherein the processing circuitry is configured to measure and ensure quality assurance.

25. The system according to claim 1, further comprising:
a product configurator, wherein
the processing circuitry is configured to assess risk parameters capturing risk-exposure of the first units as risk-exposed consumers, and
the product configurator included a machine-based exposure data intelligence enabled to automatically identify risks of the first units based on the captured risk-parameters of the first unit.

26. The system according to claim 1, wherein the adaptive learning system comprises at least one of a machine learning system and an artificial intelligence (AI) system.

27. The system according to claim 1, wherein the adaptive learning system is configured to adjust the living object or asset configuration by performing a submission transaction for creating or participating at risk-transfer structures and/or corresponding purchase or sale transactions on the digital platform.

28. The system according to claim 1, wherein the living object configuration circuit is configured to adaptively improve one of a risk-exposure measure parameter of the living object or asset or a cost of operation of the living object or asset for improving its measured risk-exposure or for using executed transactions on the digital platform.

29. The system according to claim 28, wherein the measured risk-exposure is further associated with a digital platform task.

30. The system according to claim 28, wherein the living object configuration circuit is configured to dynamically adjust the living object or asset configuration by measuring performing transaction-enabling submissions by the first unit on the digital platform.

31. The system according to claim 1, wherein
the living object or asset description circuit is further configured to interpret detected and measured conditions based on the measuring parameters, wherein the detected and measured conditions comprise at least one condition selected from conditions consisting of: an input resource for the living object or asset; a living object or asset resource; an output parameter for the living object or asset; or an external condition related to the living object or asset; and
the living object or asset model circuit is further configured to dynamically and/or in real-time update the digital twin for the living object or asset in response to the detected and measured conditions.

32. The system according to claim 1, wherein the measuring parameters comprise at least partly telematic measuring parameters measured by telematic measuring devices of the digital platform associated with the first units.

* * * * *